US007100428B1

(12) United States Patent
Dziki

(10) Patent No.: US 7,100,428 B1
(45) Date of Patent: Sep. 5, 2006

(54) METHOD AND DEVICE FOR DETERMINATION OF MOISTURE CONTENT AND SOLID STATE PHASE OF SOLIDS USING MOISTURE SORPTION GRAVIMETRY AND NEAR INFRARED OR RAMAN SPECTROSCOPY

(76) Inventor: Walter Dziki, 700 Mullady Pkwy., Libertyville, IL (US) 60048

( * ) Notice: Subject to any disclaimer, the term of this patent is extended or adjusted under 35 U.S.C. 154(b) by 0 days.

(21) Appl. No.: 10/190,357

(22) Filed: Jul. 3, 2002

Related U.S. Application Data

(60) Provisional application No. 60/387,617, filed on Jun. 11, 2002.

(51) Int. Cl.
*G01N 5/02* (2006.01)
*G01N 17/00* (2006.01)

(52) U.S. Cl. .......................................... 73/73; 73/865.6
(58) Field of Classification Search .................... 73/74, 73/73, 76
See application file for complete search history.

(56) References Cited

U.S. PATENT DOCUMENTS 5,685,192 A 11/1997 Shriner et al.
6,178,812 B1 1/2001 Kickelhain et al.

OTHER PUBLICATIONS

Columbano et al. "A study of the crystallization of amorphous salbutamol sulphate using water vapour sorption and near infrared spectroscopy," Int. J. Pharmaceutics, vol. 237, pp. 171-178 (2002).
Findlay, et al., "Utililization of Fourier transform-Raman Spectroscopy for the study of pharmaceutical crystal forms," J. Pharm. and Biomed. Anal., vol. 16, pp. 921-930 (1998).
Hogan et al. "Water sorption/desorption—near IR and calorimetric study of crystalline and amorphous raffinose," Int. J. Pharmaceutics, vol. 227, pp. 57-69 (2001).
Lane et al. "The novel combination of dynamic vapour sorption gravimetric analysis and near infra-red spectroscopy as a hyphenated technique," Int. J. Pharmaceutics, vol. 207, pp. 49-56 (2000).
Process Raman probe product description, Sentronic GmbH on-line catalog (Jan. 21, 2002) (www.getspec.com/sentronic).
Raman probe product description, Sentronic GmbH on-line catalog (Jan. 21, 2002).

(Continued)

*Primary Examiner*—Hezron Williams
*Assistant Examiner*—John Fitzgerald
(74) *Attorney, Agent, or Firm*—Leydig, Voit & Mayer, Ltd.

(57) ABSTRACT

A method and apparatus for measuring isotherms and determining solid state phase changes comprising a humidity generator having a temperature controlled internal chamber, a microbalance mounted externally to the internal chamber and a near infrared spectroscopy (NIRS) probe or Raman spectrometer probe mounted internally in the internal chamber, such that the mass of a sample suspended within the chamber and its solid state phase can be determined without disturbing the controlled environment surrounding the sample. The humidity generator includes means for controlling humidity and temperature within the internal chamber, an access port that extends into the internal chamber. The balance is situated near the port such that the balance mechanism extends within the internal chamber. The balance mechanism utilizes a means for holding a sample within the chamber such that the mass of the sample can be determined as it equilibrates to the temperature and relative humidity maintained within the internal cavity. The NIRS probe extends from a NIR spectrometer. Similarly, the Raman probe extends from a Raman spectrometer.

15 Claims, 6 Drawing Sheets

OTHER PUBLICATIONS

Raman Systems R-2001 spectrometer product description, Ocean Optics, Inc. on-line catalog, Jun. 10, 2002 (www.oceanoptics.com).
Reflection/backscattering probes product description, Ocean Optics, Inc. on-line catalog, Jun. 10, 2002 (www.oceanoptics.com).
RFP-400 series laboratory Raman probe product description, Axiom Inc. on-line catalog, Jun. 10, 2002 (www.goaxiom.com/datasheets).
RFP-500 series Process Raman probe product description, Axiom Inc. on-line catalog, Jun. 10, 2002 (www.goaxiom.com/datasheets).
SabIR User's Guide- Near Infrared fiber optic accessory product description, Magna-IR FTIR spectromers, Nicolet Instrument Corporation, 1995.
SEN-2000 Optical composition probes product description, Sensonetics Corp.on-line catalog, Jun. 10, 2002.
"Spectroscopy and light-scattering", USPC, Inc. on-line database (Apr. 1, 2002)(www.uspnf.com).
VTI Microbalance System Model MB-300 G product description (1993 Catalog, VTI Corporation).

METHOD AND DEVICE FOR DETERMINATION OF MOISTURE CONTENT AND SOLID STATE PHASE OF SOLIDS USING MOISTURE SORPTION GRAVIMETRY AND NEAR INFRARED OR RAMAN SPECTROSCOPY

CROSS REFERENCE

This application claims the benefit of U.S. provisional application No. 60/387,617, filed Jun. 11, 2002, which is incorporated by reference in its entirety.

FIELD OF THE INVENTION

The invention relates generally to generating and measuring moisture isotherms and determining the solid-state phase of solids using moisture sorption gravimetry and near infrared spectroscopy (NIRS) or Raman spectroscopy and in particular to the generation and measurement of isotherms and measurement of solid-state phase using NIRS or Raman, either simultaneously or contemporaneously, without removal of a sample from a controlled environment.

BACKGROUND OF THE INVENTION

Water vapor solid-state interactions are important in the pharmaceutical industry. These interactions are used to determine the "solid-state" stability of active pharmaceutical ingredients (API) or drug substances, finished products or drug products and raw material. Pharmaceutical solids may come in contact with water vapor during exposure upon handling and/or storage in an atmosphere of high relative humidity (RH). It is known that certain crystal forms, upon exposure to specific RH levels, convert to a different crystal form by a process known as moisture mediated crystallization. This process is especially problematic for the pharmaceutical industry as the crystal form conversion may result in a reduced shelf-life of a drug product. More importantly, the resulting converted crystal form may have different physical properties such as greater stability, reduced solubility, and hence may be less bioavailable compared to the starting or initial crystal form.

Moisture sorption gravimetry (MSG), also known as a "moisture sorption microbalance," is a widely used conventional technique that employs a microbalance in a sealed chamber at known RH levels to study water vapor solid-state interaction by measuring the sample's weight gain or loss at various RH levels. A complete cycle includes a sorption cycle from 0 to about 95% RH and desorption cycle from about 95% to 0% RH, and may take up to a few days to finish. The solid-state stability data may be estimated from isotherms generated by plotting the solid's moisture content over an RH range. The solid-state stability data may then be used to estimate shelf life and storage conditions of the API. While MSG is known as a useful technique to determine moisture content of a solid over a wide RH range, the analyst generally employs solid-state techniques to identify the crystal forms of a solid over the same RH range.

An important consideration in determining which crystal form to formulate and market is the water vapor solid-state stability. Typically, the least hygroscopic crystal form, or with the least water vapor solid-state interaction is chosen to be formulated in the marketed product. The identification of suitable solid-state phases or crystal forms is achieved by exposing samples in different relative humidity (RH) chambers over a period of time. The exposed samples are then removed from the RH chambers and then analyzed by conventional solid-state techniques, such as x-ray powder diffraction (XRPD) and mid-infrared (IR) spectroscopy to determine if any changes in the solid-state phase or crystal form had occurred in the various samples. However, these solid-state techniques have many disadvantages. Firstly, they are very time consuming, often taken up to a month to complete a RH exposure study from about 10 to 90% RH. Secondly, the techniques used require that the sample be manipulated first, such as grinding with a mortar and pestle for XRPD experiments, and grinding with potassium bromide for IR samples. Overgrinding crystalline samples has been known to change from the solid's solid-state phase to an amorphous phase, and hence may not be representative of the sample under investigation. Furthermore, an XRPD experiment may take up to about 45 minutes to complete, while the sample is exposed to ambient RH levels. During such exposure, the state or degree of hydration of the sample may change, particularly if the was initially exposed to RH levels different from ambient levels. IR experiments also have similar problems. Typically, ground IR samples are first placed in a nitrogen purged or desiccated atmosphere before an IR spectrum can be obtained. Placement of the sample in such an environment may change its state of hydration during the experiment and will not be representative of the water content or degree of hydration at the exposed RH levels. Thirdly, a complete RH exposure study requires a relatively large amount of sample that may be consumed by additional solid-state studies. For XRPD experiments, for instance, large amounts of sample (about 200–300 mg) is required for a good diffraction pattern. This is problematic when only minute samples (about 1 mg) are involved.

Near infrared spectroscopy (NIRS) is widely recognized as a technique to study solid-state phases or crystal forms of the same API. NIRS can also be used to differentiate the state or degree of hydration. NIRS uses the part of the electromagnetic spectrum between the visible and the mid infrared (mid-IR), typically between 800 to 2500 nm. NIR spectra are produced by utilizing the combination bands and overtones of the mid-IR fundamental absorption bands. Combination bands are the result of the mathematical addition of mid-IR fundamental bands. Overtones are the harmonics of the mid-IR fundamental bands. Since combination bands and overtones are typically 10 to 100 times smaller than mid-IR fundamental bands, no sample dilution is required, and little or no sample preparation is necessary, making NIRS an ideal technique in analyzing solid-state samples. Moreover, the total time of a typical NIR analysis may be as little as a few seconds.

Raman spectroscopy, unlike mid and near-infrared absorption spectroscopy, is a light scattering process in which the sample is irradiated with intense monochromatic light, usually laser light; and the light scattered from the sample is analyzed for frequency shifts in the range of about 4000 to 25 wavenumbers ($cm^{-1}$). Inelastic light scattering of monochromatic light with a sample generates Raman spectra.

In general, the Raman spectrum and the mid-infrared spectrum provide similar data, although the intensities of the spectra are produced by different molecular properties. Raman and mid-infrared spectroscopy exhibit different relative sensitivities for different functional groups, for example, Raman spectroscopy is particularly sensitive to C—S and C—C multiple bonds. In addition some aromatic compounds are more easily identified by their Raman spectra. Furthermore, symmetric vibrations and non-polar functional groups produce the most intense Raman bands. This is in contrast to mid-infrared spectroscopy where antisymmetric vibrations and polar groups produce strong absorption bands. Since Raman spectroscopy has bands in known spectra-structure correlations, it provides a direct probe of the molecular structure of a sample. Like NIR, little or no sample preparation is required for Raman analysis. Sampling could also be performed with fiber optic probes since the laser light used in Raman spectroscopy is in the near-infrared region. Water has highly intense mid- and near-infrared absorption spectra, but a particularly weak Raman spectrum, making water a Raman transparent solvent for aqueous sample analysis and solute identification and quantification.

While NIRS and Raman spectroscopy have a number of advantages that surpass the use of XRPD or mid-IR as general techniques for analyzing solid-state phase or crystal form changes as a function of RH, the analyst must still remove the sample from the RH chamber to perform NIRS or Raman, thus exposing the sample to ambient RH. Therefore, there may be no correlation to the solid-state phase at a certain RH in the MSG experiment and solid-state phase of the sample after removal from the MSG apparatus and subsequent exposure to ambient conditions.

Accordingly, there is a need in the art for a method and apparatus that allows for the accurate measurement of moisture content and solid-state phase of a sample that avoids many of the aforementioned disadvantages of conventional methods. A method and apparatus that would allow the simultaneous or contemporaneous measurement of moisture content and solid-state phase of a sample without the removal of the sample from a controlled environment would be highly desirable.

SUMMARY OF THE INVENTION

The present invention is directed to overcoming one or more of the problems set forth above. Briefly summarized, one aspect of the present invention includes an apparatus for measuring isotherms and determining solid-state phase of a sample comprising: a humidity generator having an internal cavity; a means for controlling humidity and temperature within the internal cavity; a first and second ports that extends into the internal cavity; a balance mechanism situated near the first port such that the balance mechanism extends within the internal cavity; a holding means such that the balance mechanism holds a sample within the cavity; an NIRS or Raman probe situated near the second port such that the probe extends within the internal cavity and is adjacent to the holding means; a means for determining the mass of the sample within the cavity; and a means for generating NIR or Raman spectra. An apparatus comprising a humidity generator combined with a microbalance mounted above the humidity generator's internal cavity and a NIRS or Raman probe mounted below the humidity generator's internal cavity with the three being interfaced by a general purpose computer would be such an apparatus.

The above and other objects of the present invention will become more apparent when taken in conjunction with the following description and drawings wherein identical reference numerals have been used, where possible, to designate identical elements that are common to the figures.

DETAILED DESCRIPTION OF PREFERRED EMBODIMENT(S) OF THE PRESENT INVENTION

Figure 1:
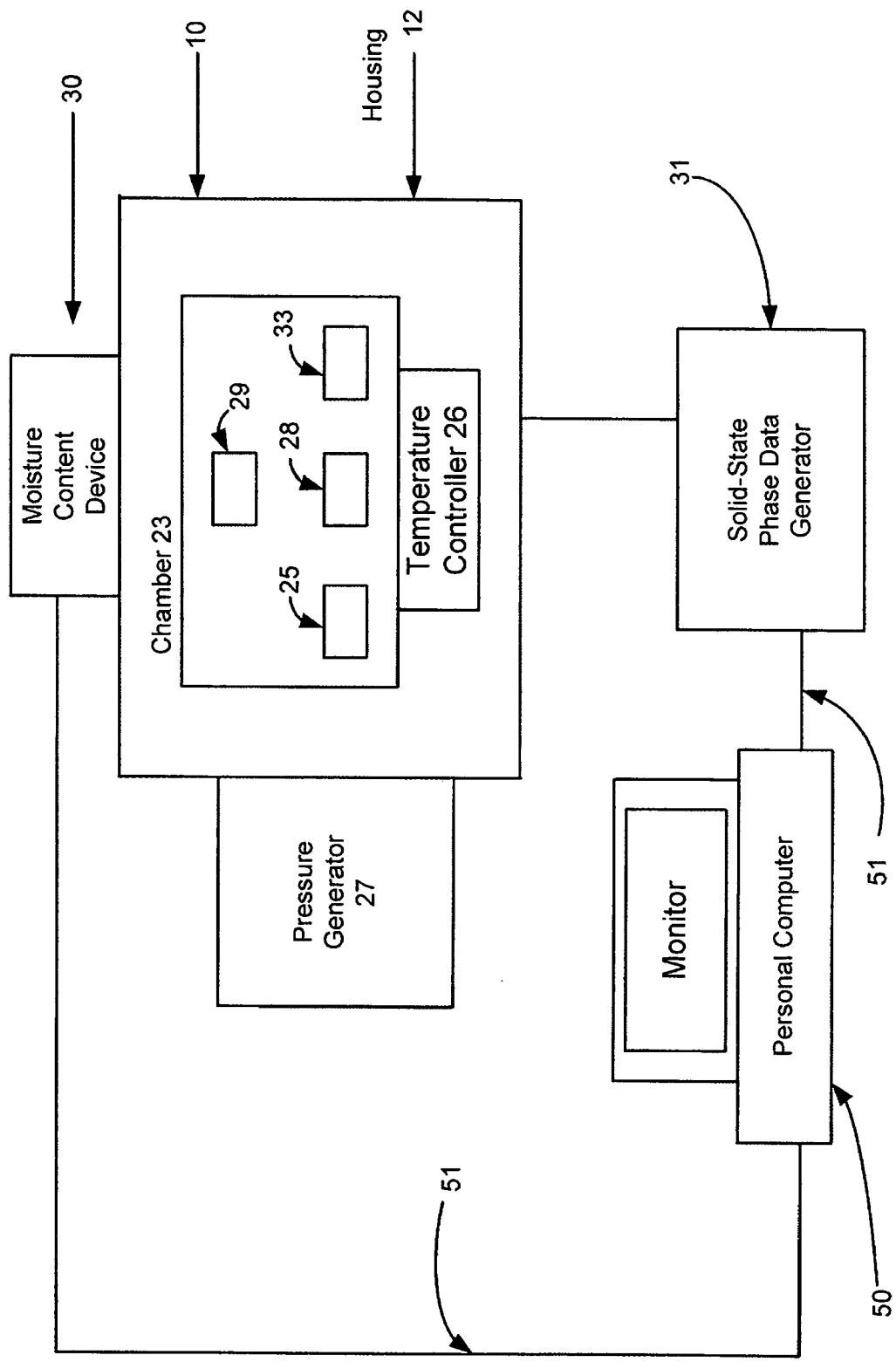
FIG. 1 is a block diagram of one embodiment of the present invention.

The present invention provides an apparatus and method to measure, simultaneously or contemporaneously, moisture content and solid-state phase of a sample without the removal of the sample from a controlled environment. In one aspect of the invention, the apparatus and method exploits known techniques, such as NIRS or Raman spectroscopy and MSG, to obtain scientifically important data from a single sample under a single controlled environment that could not be achieved by the two separate techniques independently. The invention overcomes the limitations and disadvantages of studying water vapor solid interactions currently performed in the art using these two techniques. By incorporating the two techniques in a single controlled environment, the solid-state phase and/or the state or degree of hydration of a sample can be directly and accurately determined and correlated to each RH level studied. A single apparatus that allows for the combination of analytical devices for moisture content (such as MSG) and devices for solid-state phase determination of a sample (such as NIR or Raman Spectrometer) will permit the simultaneous, rapid and accurate determination of the equilibrium moisture content (EMC, mole of water per mole of sample) and the solid-state phase associated with that EMC. This will enable analysts to rapidly and conveniently perform screening of compounds for any possible conversion to other solid-state phases, such as crystal forms. It will also enable users to determine if the moisture uptake, as observed with a weight gain, is due to loosely bound water such as on the surface, or tightly bound water such as in a cavity, pore or a water of crystallization in a single rapid procedure.

To date there has been no use of a combination of devices to measure moisture content and solid-state phase of a sample (such as MSG and NIR or Raman) in a single device to simultaneously determine percent weight gain or weight loss in moisture and the solid-state phase associated with that weight gain or weight loss. In the current practice, a sample that has gained or lost weight due to exposure at various relative humidity (RH) levels must be removed from the RH level that produced a weight change or loss. By doing so, the sample is temporarily exposed to ambient RH levels that may be different than the RH level that produced the weight gain or loss. It is known that exposed samples removed from the RH level that produced the weight change, and hence the corresponding phase change, will quickly gain or lose moisture in ambient RH levels that are very different. This weight change may also produce a change in the solid-state phase of the sample. Therefore, there may be no correlation to the solid-state phase at a certain RH level in the MSG experiment and solid-state phase of the sample after removal from the MSG apparatus and subsequent exposure to ambient conditions.

In addition, attempting to accurately determine the solid-state phase of a sample at an RH level that produced a weight change is very time consuming and exposes the sample to large differences in RH, particularly at very low and/or very high RH levels, when removing it to make the NIR spectral acquisition. For example, in order to expose a solid sample to very low RH levels, such as 10%, an appropriate saturated salt solution is prepared and the sample in an open dish is placed in a chamber with this saturated solution and allowed to reach the equilibrium moisture content. Typically for either very low, such as less than 25% RH, or very high, such as more than 60% RH levels, it may take up to about 12 hours to reach the equilibrium RH level in the chamber. However, once the sample is removed from the chamber it may immediately either gain or lose moisture and change solid-state phase upon exposure to ambient conditions, thus making an accurate determination of the solid-state phase at desired RH level impossible.

The present invention has the following advantages over the current state of technology: (1) it allows a direct determination of mass data and solid-state phase without having to remove a sample from the controlled environment; (2) it permits for the changing of a controlled environment without moving the sample; (3) it creates a system that can be controlled by an external computer which in turn allows for the sequencing of controlled environments and the determination of equilibrium points; (4) it produces more accurate results than those obtained by the prior art; (5) it allows for testing of a sample at different temperatures; (6) it allows for more accurate control of RH and temperature around the sample during mass determination and spectral acquisitions; (7) analysis time would be shorter than either XRPD or IR, with as little as less than 10 seconds per RH level; (8) no invasive sample treatment is necessary; and (9) it allows for determination of a moisture sorption isotherm and solid-state phase on a single small sample.

Figure 2:
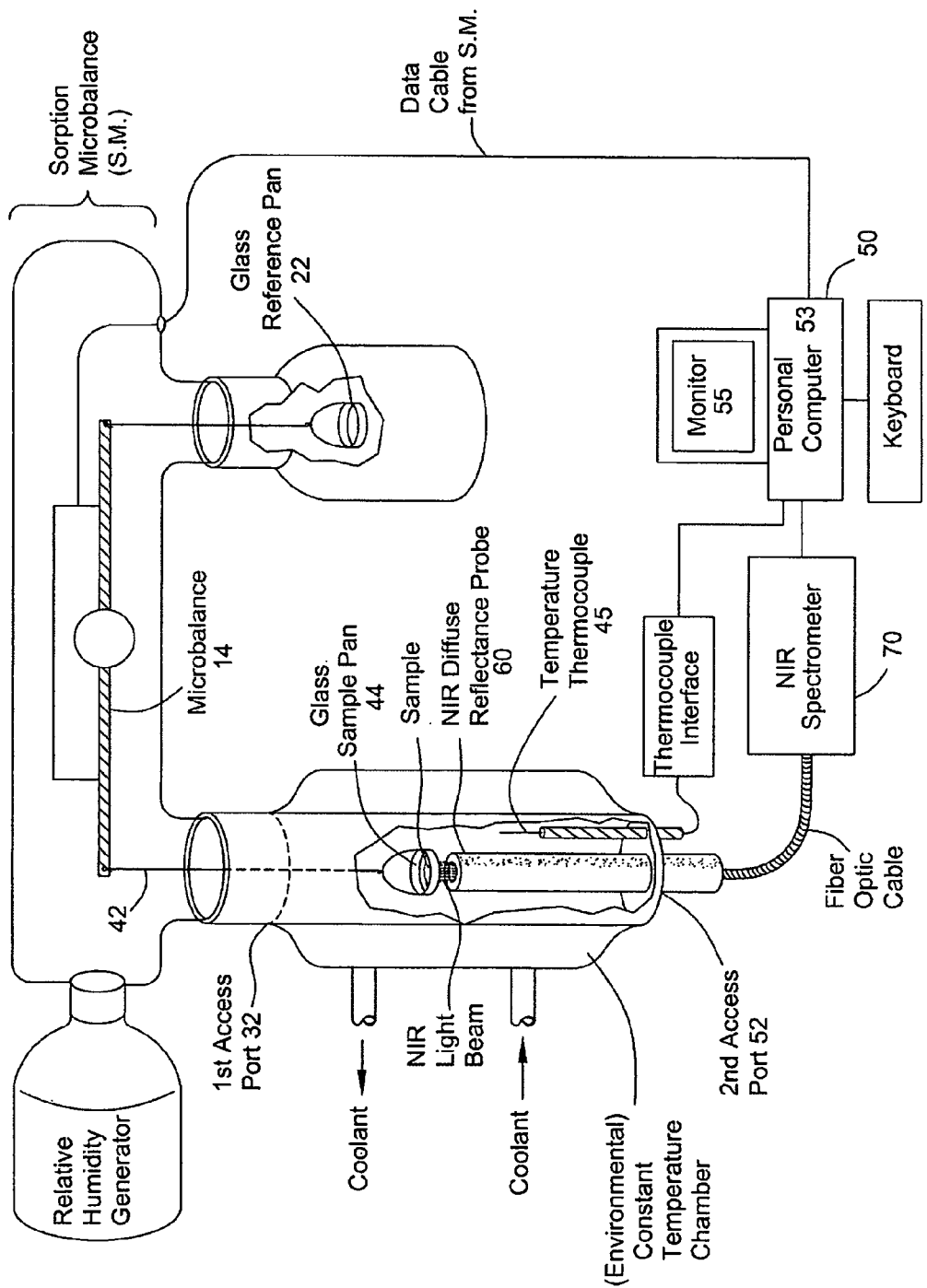
FIG. 2 is a block diagram of another embodiment of the present invention using a NIR spectrometer.

The present invention relates to a technique for obtaining moisture isotherms and determining the solid-state forms of test samples to a high degree of accuracy and precision. Referring to FIG. 1, there is shown a block diagram of one embodiment of the present invention. Device 10 shown in FIG. 1 is used to practice this technique. A sample is placed within chamber 23 located in housing 12. The environment of the chamber is controlled by an environmental control device. In one embodiment, as shown in FIG. 1, the environmental control device may comprise a temperature controller 26 and a pressure generator 27. The temperature controller 26 may control the temperature of the chamber. In one embodiment, the temperature controller 26 may comprise a water jacket (as shown in FIG. 2). The water jacket may allow a coolant (such as water) to flow on the exterior of chamber 23. The temperature controller 26 may be controlled by computer 50. As shown in FIG. 2, computer 50 may include a PC 53 and a monitor 55. Alternatively, the temperature controller 26 may be controlled by a dedicated processor. The pressure generator 27 may include a vacuum pump. Similar to temperature controller 26, pressure generator 27 may be controlled by computer 50 or by a dedicated processor. Alternatively, the environmental control device may comprise a humidity generator (not shown) such as a device which produces a water vapor in chamber 23. Chamber 23 may further include sensors for the environmental control device. One sensor may comprise a temperature sensor 25 which provides data regarding the temperature in chamber 23. As shown in FIG. 2, the temperature sensor may comprise a temperature thermocouple 45. Another sensor may comprise a pressure sensor 28. Pressure sensor 28 provides data to pressure generator 27 regarding the pressure in chamber 23. While the pressure sensor is shown in FIG. 1 as being located inside chamber 23, the pressure sensor may be outside chamber 23 but within housing 12. FIG. 1 further includes a moisture content device 30. The moisture content device generates data regarding the moisture content of a sample which is placed in chamber 23. The data is analyzed in order to determine the moisture content. In one embodiment, computer 50 is used to analyze the data. In an alternate embodiment, a separate processor may be used. Moisture content device includes at least a portion of the device 29 within chamber 23. In one embodiment as shown in FIG. 2, the moisture content device comprises a sorption microbalance. Further, the portion of the device 29 within chamber 23 is the glass sample pan 44 and a portion of wire 42. Other means for generating moisture content data may be used. FIG. 1 further includes Solid State Phase Data Generator 31. As discussed above, the present invention provides an apparatus and method to measure moisture content and solid-state phase of a sample without the removal of the sample from a controlled environment. The Solid State Phase Generator 31 uses a sensor 33 to generate data from the sample to determine the solid-state phase of the sample. As shown in FIG. 1, the sensor 33 is located within chamber 23. The data may then be analyzed, either by an operator or by a processor (such as computer 50), to determine the solid-state phase of the sample. In one embodiment, as discussed in FIG. 2, the Solid State Phase Generator comprises a NIR spectrometer 70. Data may be generated using a sensor, such as a NIR diffuse reflectance probe 60, which is then sent to NIR spectrometer 70. In an alternate embodiment, data may be generated using a Raman Spectrometer. The data generated may then be analyzed by computer 50 or by an operator to determine the solid-state phase of the sample. As shown in FIG. 1, wires 51 connect the devices to computer 50. In an alternative embodiment, the connections may be wireless.

Referring to FIG. 2, there is shown a block diagram of another embodiment of the present invention using a NIR spectrometer. The sample may be suspended above an environmental chamber 23 which is precisely controlled by environmental control device such as temperature controller 26 and pressure generator 27, as shown in FIG. 1. The sample, hanging within the environmental chamber 23 is connected to the microbalance 14 via a hangdown wire 42 which passes through a first access port 32 in the environmental chamber 23. The environmental control device produces a precisely controlled relative humidity which is supplied to the temperature controlled environmental chamber 23. The sample is held by a holding means 44 that is invisible or transparent to NIR wavelengths such as a glass sample pan. The mass of the sample hanging within this controlled environment can thus be continuously measured via the recording microbalance 14, which uses microbalance reference pan 22. Adjacent to the holding means 44 is an NIR diffuse reflectance probe 60 which passes through a second access port 52 and is positioned below the environmental chamber 23.

Sorption moisture gravimetry (MSG) is a technique that measures the % weight change of a sample versus % relative humidity (RH). MSG utilizes a microbalance in an environmental chamber connected to a RH generator. RH can be generated either by a vacuum system or by a flow system. The vacuum system generates the partial pressure of water in a vacuum to produce the desired % RH level or whereas a flow system operates at one atmosphere pressure using a combination of water vapor and a dry inert gas, such as nitrogen, to generate the desired % RH level. Both types of MSG systems are commercially available as bench top units with about 2.5 to 4 square feet footprint and may be used in the MSG-NIRS system of the invention. Commercially available MSG systems include a VTI Corporation model SGA-100 Symmetrical Gravimetric Analyzer or a MB-300G Gravimetric Sorption Analyzer From VTI Corporation:

The SGA-100 Symmetrical Gravimetric Analyzer is a continuous vapor flow sorption instrument for obtaining water and organic vapor isotherms at temperatures ranging from 0° C. to 80° C. at ambient pressure. As a result of its symmetrical design (both the sample and the reference side of the microbalance are subjected to identical temperature, relative humidity and flow rate), this instrument achieves great accuracy and stability. Another benefit of this design is that it allows the analyst to perform absolute or differential adsorption experiments. In addition to generating isotherms, heats and kinetics of adsorption and hydrate formation can also be studied. The core of the instrument is an isothermal aluminum block containing the sample chamber, which permits very tight control of temperature and RH at the sample. The temperature within the block is kept stable by a constant temperature bath capable of temperature control within 0.01° C. Because of the easy access to the sample and the absence of glass hang-down tubes, this instrument is very easy to operate and highly reliable. The SGA-100 is also very compact, with a footprint of only 18"×20".

The MB-300G Gravimetric Sorption Analyzer was designed specifically for adsorption studies in applications that require sub-ambient adsorbate pressures, and is specifically suited for experimental situations where sample drying is critical. This instrument also obtains low temperature isotherms and is very useful when several different adsorbates must be used routinely, because it provides very thorough pre-experimental outgassing. The microbalance is isolated at a constant temperature for stability and experimental reproducibility. The sample chamber is controlled within 0.01° C. at temperatures ranging from 0° C. to 80° C. A mechanical two-stage rotary pump is supplied for standard vacuum requirements, pressures down to $10^{-3}$ torr. If a higher vacuum is required, diffusion, turbomolecular or molecular drag pumps provide vacuum down to $10^{-6}$ torr.

The preferred embodiment of the present invention employs a VTI Corporation model MB300G sorption microbalance that has been modified to allow for incorporation and proper positioning of a NIR diffuse reflectance probe. The VTI sorption microbalance MB 300G model was designed as a bench-top unit that includes a humidity generator 12, a microbalance, and a temperature regulator. Typically, the constant temperature chamber 23 from VTI have a first access port 32 on the environmental chamber 23 to make mass determinations on a sample. The present invention is created with the introduction of a second access port 52 on the environment chamber that is utilized for making solid-state phase determinations on a sample. The existence of the first port 32 allows the microbalance to be positioned above the internal cavity of the environmental chamber 23 so that the hangdown wire 42 from the balance passes through the first access port 32 and into the internal cavity 23. This in turn allows for measurement of the sample mass within the confines of the internal cavity. The existence of the second port 52 allows a NIR probe to be inserted into the internal cavity of the environmental chamber 23 and positioned below the holding means 44 for holding the sample. This allows for solid-state phase determinations of the sample via NIR spectroscopy within the confines of the internal cavity.

The VTI microbalance system is controlled through an external computer 50 to control functions such as temperature, pressure, and RH conditions, to sequence temperature and RH conditions inside the chamber, and to perform calculations. External equipment may be interfaced via an RS-232 interface and the control capability of sequential setpoints can be accomplished through the external computer via the RS-232 interface port. The computer monitors and controls the temperature and humidity within the cavity 23 and the operation of the environmental control device, and the NIR spectrometer. The settings may be controlled through an external computer 50. Therefore, the preferred embodiment of the present invention employs an external computer 50 to sequence temperature and RH conditions within the chamber via an RS-232 interface.

While the preferred embodiment employs a VTI sorption microbalance system, other devices for generating precisely controlled, variable, RH and temperature environments could be used. Environmental chambers, which control the environment via a steam generator, could also be employed. These microbalance systems may have an on-board computer and control system to perform calculations and control functions. The on-board computer system monitors and controls the temperature and humidity within the cavity 23 and the operation of the humidity generator 12 itself. The settings may be controlled either through an on-board computer or through an external computer 50. External equipment may be interfaced via an RS-232 interface. The control capability of sequential setpoints can be accomplished through an external computer via the RS-232 interface port. Preferably, these devices employ an external computer 50 to sequence temperature and RH conditions within the chamber via an RS-232 interface. The preferred embodiment employs VTI sorption microbalance system to achieve precise RH control over a wide range of humidities and temperatures.

Figure 3:
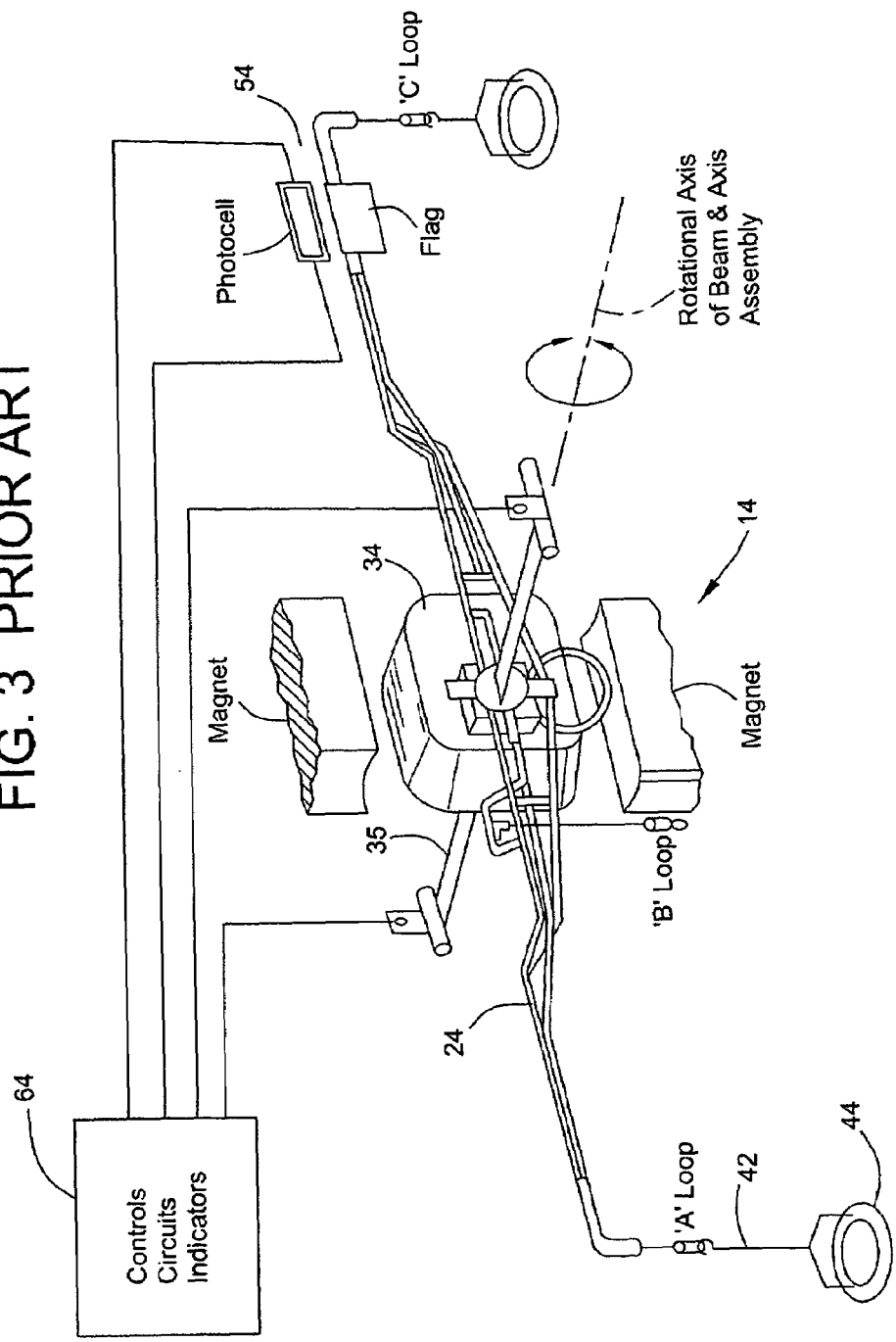
FIG. 3 is a perspective view of the microbalance used by the present invention.

Referring now to FIG. 3, a magnified view of the microbalance as used by the preferred embodiment of the invention can be seen. The microbalance 14 used by the preferred embodiment of the present invention is a Cahn D-200 recording microbalance, which can accommodate masses up to 3½ grams and as small as 0.1 micrograms. The microbalance 14 is contained within dome 13. The unit is positioned above the cavity 23, and is isolated from external building vibration. A flexible material 15 is used to connect the balance/dome unit 13 to the internal cavity 23 such that the environment inside the test chamber is preserved and the microbalance is not affected by any vibration from the humidity generator 12. The microbalance 14 is divided into two sections. One section is a control unit 64 comprised of electronics and the other section is a Weighing Unit which detects the actual mass of a sample. The Cahn-D200 microbalance is also capable of measurements under high vacuum which is useful for determining the dry mass of the sample. The balance mechanism operates as a force-to-current converter. The unit consists of: 1) a balance beam 24 pivoting about the center of a taut ribbon; 2) a torque motor coil 34 located in a permanent magnetic field and also mounted to the taut ribbon 35; 3) sample suspension fixtures 44; 4) a beam position sensor system 54; and 5) control, circuitry and indicators 64. The microbalance 14 operates by having the torque motor 34 keep the balance beam in a reference position. This is accomplished by generating currents in the torque motor coil 34 in response to weight being placed on the sample suspension fixture 44 on the balance beam 24. The more force placed on the sample suspension fixtures 44 the more force is required by the torque motor coil 34 to keep the balance beam 24 in place.

Other microbalances, such as a Cahn C-2000 with a strip chart readout (not shown), or other microbalances that give a digital readout could conceivably be substituted for the Cahn D-200. Where the D-200 requires a manufacturer specified personal computer, other microbalances may not. These microbalances still result in a visually discernible output which can be correlated by an operator to the relative humidity within the humidity generators internal cavity.

NIRS may be performed either by dispersive or Fourier transform (FT) based technology. Both are small bench top units, typically with about a 2 to 4 square feet footprint. Dispersive NIR technology is about 35 years older than FT-NIR technology but has lower spectral resolution. Typically, dispersive NIR spectrometers can only achieve spectral resolution of about 50 wavenumbers (cm−1), whereas FT-NIR spectrometers can go down to 1 wavenumber resolution. In addition, FT-NIR spectrometers have faster acquisition times than dispersive NIR spectrometers. Typical FT-NIR spectrometer acquisition times are less than one minute for high resolution (<8 wavenumber) spectra. Crystalline solid-state samples typically have smaller bandwidths than corresponding amorphous solid-state samples. Although dispersive NIR spectrometers can be used in a SMG-NIRS, FT-NIR spectrometers are preferred since they have the high spectral resolution that is necessary for studying crystalline and amorphous solid-state phases and phase changes. A typical FT-NIR system is either a Thermo Nicolet Avatar 360N or Anataris model with a SabIR NIR diffuse reflectance probe.

Raman spectroscopy employs a laser excitation source to induce scattering from the targeted sample. The spectrometer is used to detect this low-level return signal to identify the sample makeup. The popularity of Raman is growing over the competitive IR analysis technique because no sample preparation is required and silica fiber optics and detectors are efficient and low in the VIS and NIR regions. There are several popular laser excitation wavelengths such as 532, 632, 670, 785 and 1064 nm. These Raman spectrometers are often interfaced with Raman fiber optic probes. Raman spectrometers and Raman fiber optic probes are commercially available. Suitable, but non-limiting, examples of Raman spectrometers and Raman fiber optic probes include InPhotonics RS 2000 High Resolution Raman spectrometer in combination with RamanProbe™ fiber optic probe (available from InPhotonics, Inc.; Raman-Rxn systems including a fiber optic probehead from Kaiser Optical Systems, Inc., a Rockwell Collins Company; and Raman spectrometers and fiber optic Raman probes from Sentronic GmbH, Ocean Optics, Inc.; Avantes, StellarNet, Inc., Renshaw, Inc., and Nicolet.

To measure the moisture content ("MC") and the solid-state phase of a material using the preferred modified VTI sorption microbalance system MB300G, a sample (about 10 mg) is hung from the holding means 44 such as a tarred, clean, transparent glass sample pan which is attached to one end of a wire like balance beam 24. The hangdown wire attached to the holding means is long enough to pass down through the first access port 32 and into the temperature controlled test chamber 23. Means for sensing the temperature of chamber 23 such as a temperature thermocouple 45 or a temperature sensing device is generally present anywhere near the sample to allow for determination of temperature of the sample environment. An NIR probe 60, such as a Nicolet Corporation SabIR NIR diffuse reflectance probe, is inserted into the second access port 52 of chamber 23, preferably adjacent to a temperature thermocouple 45, and the tip of the probe is positioned below the sample suspension fixture 44 such that the probe tip is close to but does not touch the fixture 44 such that NIR spectra can be obtained. If the probe tip is positioned beyond an acceptable range, no spectral acquisitions may be obtained. Generally, the probe tip is position about 2 to 5 mm below the bottom surface of fixture 44. Once the probe has been properly positioned, the probe is secured in place using a fastening means such as a rubber or neoprene O-ring. For the VTI model MB300G, the height of the NIR probe is generally adjusted such that it is between 1 and 30 mm below the height of fixture 44. The NIR probe is connected to a NIR spectrometer 70. Controlled temperature and RH air is flowed over the sample. The balance beam 24 is attached to a sensitive recording balance as previously described. The temperature around the balance is strictly controlled and the balance itself is isolated from vibration. This setup allows for accurate measurement of the sample's mass and determination of solid-state phase as it equilibrates to the set RH and temperature. Following equilibration of the sample, the RH is changed (raised or lowered) and mass and NIR spectral data accumulated at the new RH value. Therefore a moisture isotherm can be generated on a single sample and the equilibrium mass and solid-state phase information obtained without having to remove the sample from the temperature and RH controlled environment.

To determine moisture content, the sample's wet weight and dry weight must be determined. Moisture content (MC), dry basis, is defined by the Equation 1:

$$MC(\text{dry basis}) = 100 \times (M_{wet} - M_{dry})/M_{dry}$$

where $M_{wet}$ is the mass of the sample at the storage RH; and $M_{dry}$ is the mass of the sample with all of the water removed or at 0% RH.

Dry weight can be determined by drying samples using microwave or infrared treatment, heating in an oven, flowing a dry gas such as nitrogen over the sample, evacuation of a sample, or a combination of these techniques such as heating while evacuating. As the Cahn microbalances are capable of operation under vacuum and low to medium vacuums have been shown to be non-detrimental to test samples, determination of the dry mass via evacuation under controlled temperatures is the preferred method of this invention.

The wet weight is determined by putting a sample in a temperature controlled RH environment and weighing the sample when it reaches equilibrium with the surrounding environment. Previous experiments have shown that problems exist in weighing a sample after it has been removed from a first controlled RH condition and placed in a second controlled RH condition because the sample begins to equilibrate to the second RH condition immediately being placed in the second controlled condition. Therefore, making the measurement of the mass of the sample without removing the sample from the controlled environment is preferred. The present invention allows for the measurement of a sample's mass at equilibrium without removing it from the controlled environment. Furthermore, a complete isotherm can be generated on a single sample by alternating the environment around the sample without removing it from the test chamber.

Generation of a complete isotherm and NIR spectra for a given sample requires mass and spectral data at many RH values. This fact means that either a large number of RH controlled devices are required or that a few devices be used but the RH would change after each reading. Requiring an operator to change the RH after each reading can be extremely labor intensive. By interfacing the microbalance, the humidity generator, and the NIR spectrometer via an external computer, the RH can be altered and the resulting equilibrium mass of the sample determined and spectral acquisitions collected for numerous choices of controlled environments. The computer sets the RH value, records mass data as a function of time, determines when the sample is equilibrated, and ramps the generator to the next RH.

Figure 4:
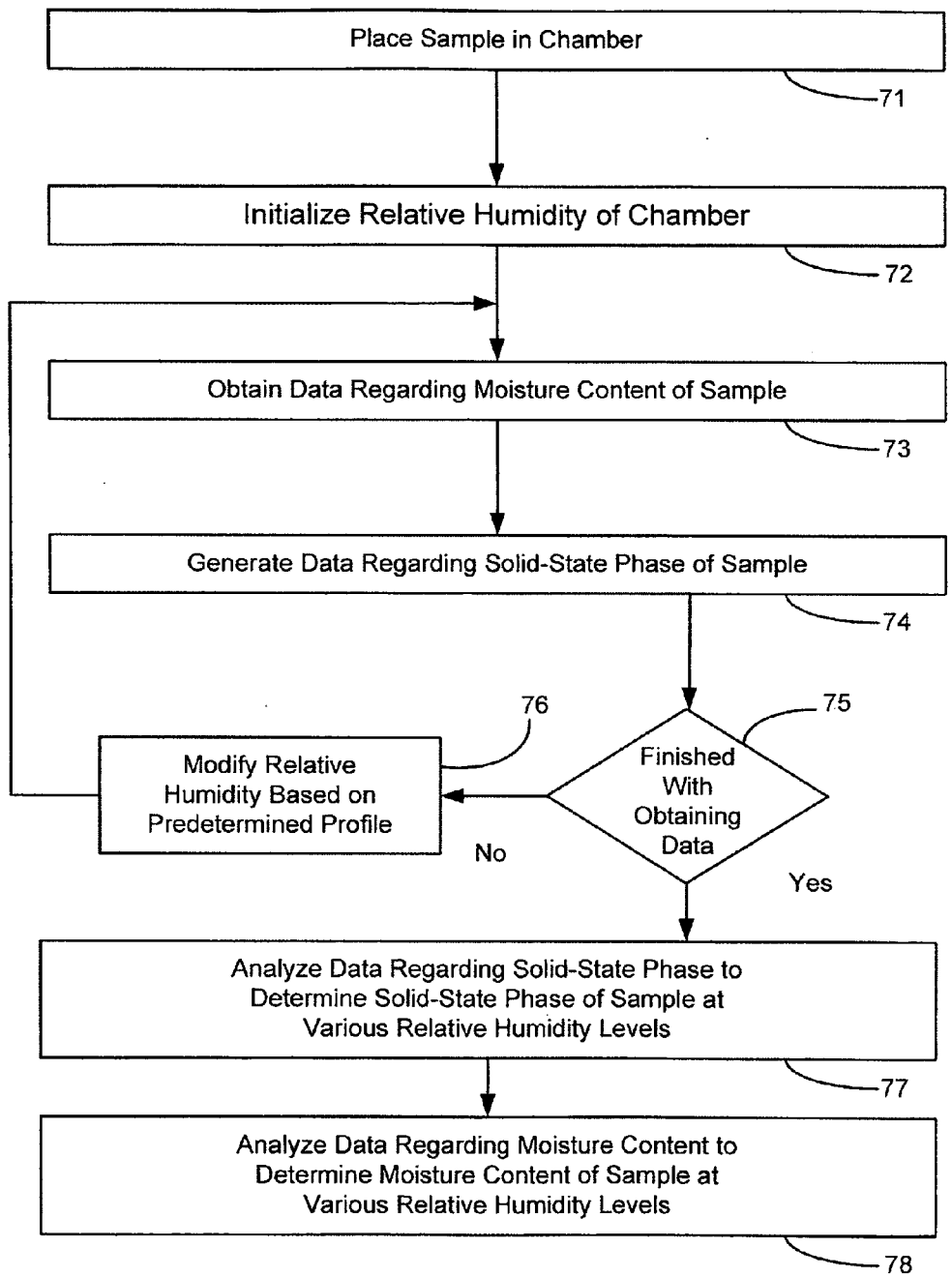
FIG. 4 is a flow chart of one embodiment of the present invention.

Referring to FIG. 4, there is shown a flow chart for another embodiment of the invention. As shown at block 71, the sample is placed in chamber 23. The chamber is initialized for a predetermined relative humidity, as shown at block 72. The relative humidity in the chamber may be modified by modifying the pressure and/or temperature of the chamber, for example. Data is obtained regarding moisture content of the sample, as shown at block 73. In one embodiment, data is obtained by using a microbalance. The microbalance includes a glass pan 44, as discussed above, for holding the sample, with the glass pan being inside the chamber. Data is generated regarding the solid state phase of the sample, as shown at block 74. In one embodiment, the data may be generated by using a near infrared (NIR) spectroscopy device. The NIR spectroscopy device may include a probe with at least a portion of the probe being within chamber 23. Alternatively, the data may be generated by using a Raman Spectrometer and probe.

Data regarding moisture content may be obtained either before, after or contemporaneously with generating data regarding the solid state phase of the sample. It is then determined whether the system is finished with obtaining data, as shown at block 75. If it is not, the relative humidity is modified based on a predetermined profile, as shown at block 76. This predetermined profile may be stored in computer 50. Thereafter, the loop is re-executed, obtaining data regarding moisture content and generating data regarding solid state phase. As shown at block 77, when the program is finished obtaining data, the data regarding the solid state phase is analyzed (either by the operator manually or by the computer 50) to determine the solid state phase of the sample at the various relative humidities. As shown at block 78, the data regarding moisture content is analyzed to determine the moisture content of the sample. In one aspect, this step of analyzing comprises using a computer (such as computer 50) to analyze the data regarding moisture content to determine the moisture content of the sample.

Figure 5A:
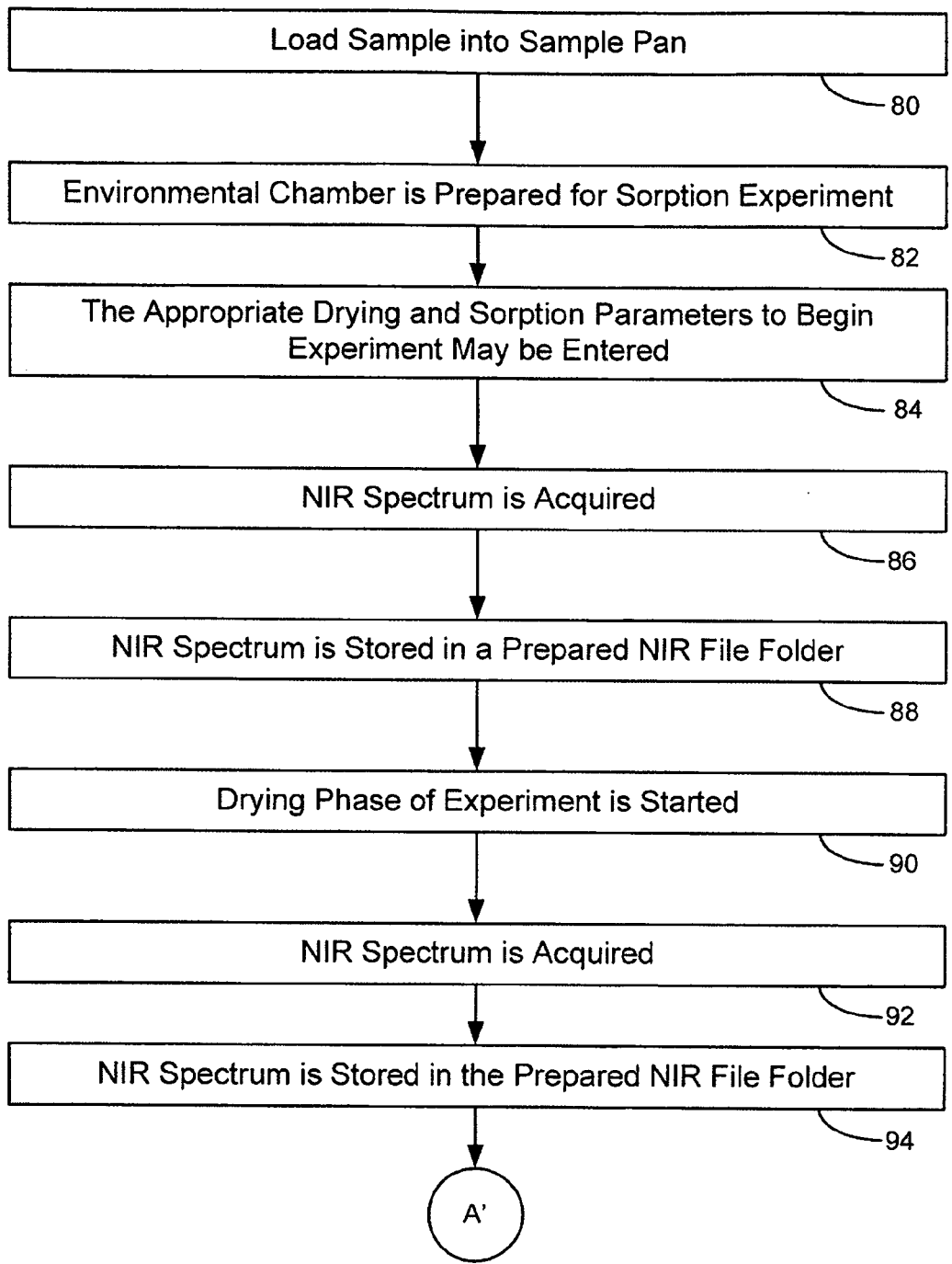
FIGS. 5A–B are a flow chart of another embodiment of the present invention.
Figure 5B:
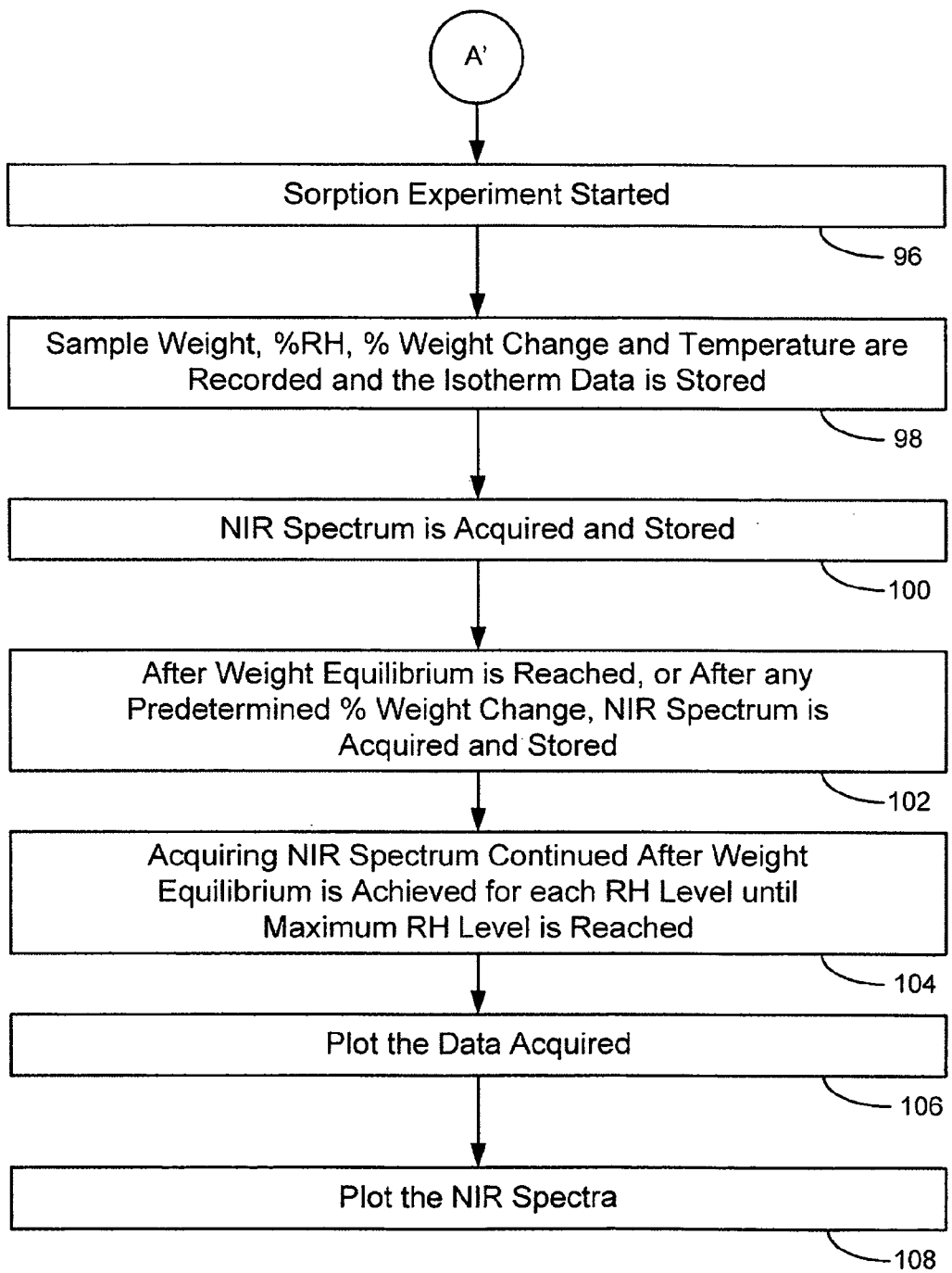

Referring to FIGS. 5A–B, there is shown a flow chart for another embodiment of the invention. As shown at block 80, the sample is loaded sample in sample pan 44. The environmental chamber is prepared to begin the sorption experiment, as shown at block 82. The appropriate drying and sorption parameters to begin the experiment may be entered, as shown at block 84. Alternatively, the appropriate drying and sorption parameters may be accessed from computer 50. As shown at block 86, the NIR spectrum of the sample is acquired. The NIR spectrum is stored in a prepared electronic NIR file folder, as shown at block 88. The drying phase of the experiment is started, recording the sample weight, % RH level, % weight change and temperature and storing the isotherm data in a prepared electronic SMG (sorption microbalance gravimetry) data file, as shown at block 90. After the sample is sufficiently dried, an NIR spectrum is acquired, as shown at block 92. The NIR spectrum is stored in the prepared electronic file folder, as shown at block 94. The sorption experiment is started, typically 0% RH (relative humidity), as shown at block 96. While the data for the solid-state phase of a sample is acquired first and then the data for the moisture content is acquired, the data acquisition may be reversed (first obtaining data for the moisture content and then data for the solid-state phase). The sample weight, % RH level, % weight change and temperature is continued to be recorded and the isotherm data is stored in a prepared electronic SMG data file, as shown at block 98. The NIR spectrum is acquired and stored in the prepared electronic file folder, as shown at block 100. After weight equilibrium is reached for each desired RH level, typically every 5% RH units, or after any predetermined % weight change, an NIR spectrum is acquired and stored in the prepared electronic file folder, as shown at block 102. The process of acquiring NIR spectra is continued after weight equilibrium is achieved for each desired RH level until the desired maximum RH level is reached, as shown at block 104. If a desorption experiment is desired after the sorption experiment, the process of acquiring NIR spectra is acquired after weight equilibrium is achieved for each desired RH level until the desired minimum RH level is reached, as shown at block 106. Optionally, a plot of the sorption/deorption isotherm data, typically % weight change versus RH may be generated, displaying the equilibrium moisture content level for each desired % RH level, every 5% RH units over a range of 0% to 95% RH, as shown at block 106. Moreover, optionally, a separate plot may display the corresponding NIR spectra at each equilibrium moisture content level for each desired % RH level, as shown at block 108. The NIR spectral plot may be a direct correlation of the solid-state phase at each equilibrium moisture content level.

The preferred embodiment of the interface program allows the operator to specify 1) test parameters including RH, temperature, and flow rate inside the internal cavity, 2) number of conditions per run, 3) the data logging interval, 4) the minimum time that the humidity generator must maintain each specified environmental condition, 5) the equilibrium criteria, as defined by a mass change per time, that must be met, once the minimum time criteria has been satisfied, before the computer can sample the humidity generator to the next specified environmental condition, 6) number of NIR spectral acquisitions per run, and 7) the maximum time the humidity generator is to maintain the environmental condition even if the equilibrium criteria is not satisfied. The interface program also creates data files if 1) mass of the sample and humidity generator conditions and system information versus time, as specified by the data logging interval and 2) equilibrium values of mass and humidity generator variables as defined at the time directly before the generator is sampled to the next specified environmental condition.

Therefore, use of an external computer to interface the system allows a complete isotherm to be generated and spectral acquisitions to be made on a single sample without the need for extensive operator intervention, and as such is a preferred embodiment of the invention.

Even when taking precautions for many factors, the moisture content measurement is usually somewhat irreproducible. Most of the noise in the measurement comes from control of temperature and RH around the sample. The configuration of the present invention alleviates many of the problems that existed in the prior art.

The present invention, while being created to measure isotherms and determine the solid-state phases of active pharmaceutical ingredient samples, is useful for a number of other industries, including food, agriculture, and consumer products. Photographic film and film constituents fall within this group of industries.

The invention has been described with reference to a preferred embodiment. However, it will be appreciated that variations and modifications can be effected by a person of ordinary skill in the art without departing from the scope of the invention.

PARTS LIST

10 Device
12 humidity generator
14 microbalance
23 cavity
24 balance beam
32 access port
34 torque motor coil
35 torque ribbon
42 hangdown wire
44 sample suspension fixture
45 temperature thermocouple
50 Computer
51 wires
54 beam position sensor
60 NIR probe
64 control circuitry and indicators
70 NIR spectrometer

What is claimed is:

1. A device for measuring isotherms and for determining the solid-state phase of a sample comprising:
  a humidity generator having an internal cavity;
  means for changing and controlling humidity and temperature within the internal cavity to establish a sequence of environments each potentially having a different humidity and a different temperature for each environment;
  a temperature sensor that extends within the internal cavity and is positioned near the sample so that the sensor measures the temperature surrounding the sample;
  first and second ports that extends into the internal cavity;
  a balance, having a balance mechanism with means for holding a sample, situated near the first port such that the balance mechanism extends within the internal cavity;
  a Raman probe situated near the second port such that the probe extends within the internal cavity and is positioned near the sample so that one or more Raman spectra from said sample may be acquired;
  means for determining the mass of a sample within the internal cavity via the balance mechanism for each environment;
  means for acquiring and analyzing one or more Raman spectra;
  means for determining a final mass for each environment where a calculated change in the mass of the sample effectively drops below a predetermined value;
  means for displaying humidity and temperature within the cavity, and the final mass in a visually discernible manner; and
  means for sequencing through the sequence of environments, whereby isotherms are measured and associated solid-state phases of the sample are determined.

2. The device of claim 1 wherein the balance further comprises a microbalance.

3. The device of claim 1 wherein the means for determining the mass of the sample further comprises a means for continuously monitoring the mass of the sample.

4. The device of claim 1 wherein the humidity generator further comprises a relative humidity generator that allows selection of humidity of a predetermined amount.

5. The device of claim 1 wherein the means for acquiring and analyzing one or more spectra comprise a Raman spectrometer.

6. The device of claim 1 further comprising means for determining when the sample has reached equilibrium within the controlled environment.

7. The device of claim 1 further comprising means for maintaining the test chamber at a constant temperature and RH until the sample reaches equilibrium with the environment.

8. The device of claim 1 further comprising means for adjusting the environment within the test chamber and for determining the mass of the sample continuously until equilibrium is again reached.

9. The device of claim 1 wherein the means for changing and controlling humidity and temperature within the internal cavity to establish a sequence of environments comprises a computing device external to the humidity generator.

10. The device of claim 9, wherein the computing device further comprises at least a portion of the means for: determining the mass of a sample within the internal cavity via the balance mechanism for each environment; acquiring and analyzing one or more Raman spectra; determining a final mass for each environment where a calculated change in the mass of the sample effectively drops below a predetermined value; displaying humidity and temperature within the cavity, and the final mass in a visually discernible manner; and sequencing through the sequence of environments.

11. The device of claim 10, wherein the computing device is connected at least indirectly to the humidity generator, temperature sensor, balance, and Raman probe via one or more wired connections.

12. The device of claim 11, wherein the one or more wired connections comprise an RS-232 connection.

13. The device of claim 11, wherein the computing device is connected at least indirectly to the humidity generator, temperature sensor, balance, and Raman probe via one or more wireless connections.

14. A device for measuring isotherms and for determining the solid-state phase of a sample comprising:
  a humidity generator having an internal cavity for containing the sample and having therein a mass measurement sensor and a Raman probe; and
  a controller for changing and controlling humidity and temperature within the internal cavity to establish a sequence of environments each potentially having a different humidity and a different temperature, and for determining the mass of the sample via the mass measurement sensor for each environment, and for acquiring and analyzing one or more Raman spectra for the sample relative to each environment via the Raman probe, and for sequencing through the sequence of environments, whereby isotherms are measured and associated solid-state phases of the sample are determined.

15. The device of claim 12, wherein the controller comprises a computing device external to the internal cavity.

* * * * *